US010544437B2

(12) United States Patent
Han et al.

(10) Patent No.: US 10,544,437 B2
(45) Date of Patent: Jan. 28, 2020

(54) MICROBIAL ERGOTHIONEINE BIOSYNTHESIS

(71) Applicant: Conagen Inc., Bedford, MA (US)

(72) Inventors: Jixiang Han, Maryland Heights, MO (US); Hui Chen, Bedford, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 15/307,491

(22) PCT Filed: Apr. 28, 2015

(86) PCT No.: PCT/US2015/027977
§ 371 (c)(1),
(2) Date: Oct. 28, 2016

(87) PCT Pub. No.: WO2015/168112
PCT Pub. Date: Nov. 5, 2015

(65) Prior Publication Data
US 2017/0051325 A1 Feb. 23, 2017

Related U.S. Application Data

(60) Provisional application No. 61/985,778, filed on Apr. 29, 2014.

(51) Int. Cl.
*C12P 17/10* (2006.01)
*C12N 15/52* (2006.01)
*C12P 13/04* (2006.01)

(52) U.S. Cl.
CPC .............. *C12P 17/10* (2013.01); *C12N 15/52* (2013.01); *C12P 13/04* (2013.01)

(58) Field of Classification Search
CPC ........... C12N 15/52; C12P 13/04; C12P 17/10
See application file for complete search history.

(56) References Cited

U.S. PATENT DOCUMENTS

| 5,438,151 | A | 8/1995 | Yadan et al. |
| 6,326,034 | B1 | 12/2001 | Mirsky et al. |
| 7,767,826 | B2 | 8/2010 | Trampota |
| 8,399,500 | B2 | 3/2013 | Erdelmeier |
| 2015/0225755 | A1* | 8/2015 | Liu .................. C12N 15/52 548/324.1 |
| 2017/0051325 | A1 | 2/2017 | Han et al. |

FOREIGN PATENT DOCUMENTS

| CN | 103184246 A | 7/2013 |
| CN | 103734022 A | 4/2014 |
| WO | WO 2008/010096 A2 | 1/2008 |
| WO | WO 2014/100752 A1 | 6/2014 |
| WO | WO 2015/168112 A1 | 11/2015 |

OTHER PUBLICATIONS

Emani et al., Antimicrobial Agents and Chemotherapy 57(7):3202-3207; published ahead of print on Apr. 29, 2013.*
Branden et al., Introduction to Protein Structure, Garland Publishing Inc., New York, p. 247.*
Sadowski et al. Current Opinion in Structural Biology 19:357-362, 2009.*
Sousa et al., Microbiology 148(Pt5):1291-1303, 2002.*
Seffernick et al., J. Bacteriol. 183(8):2405-2410, 2001.*
Witkowski et al., Biochemistry 38:11643-11650, 1999.*
Helbig et al., Journal of Bacteriology 190(15):5431-5438, 2008.*
Yurimoto et al., International Journal of Microbiology 2011:1-8, article ID 101298, 2011.*
Grant et al., Curr Genet 29:511-515, 1996.*
International Search Report and Written Opinion dated Aug. 12, 2015 for Application No. PCT/US2015/027977.
International Preliminary Report on Patentability dated May 3, 2016 for Application No. PCT/US2015/027977.
GenPept Submission; NIH/NCBI, EGTB_MYCS2. Accession No. A0R5N0.1. Fleishmann et al., Jun 24, 2015. 4 pages.
GenPept Submission; NIH/NCBI, EGTC_MYCS2. Accession No. A0R5M9.1. Fleishmann et al., Jun 24, 2015. 4 pages.
GenPept Submission; NIH/NCBI, EGTD_MYCS2. Accession No. A0R5M8.1. Fleishmann et al., Jun 24, 2015. 9 pages.
GenPept Submission; NIH/NCBI, EGTE_MYCS2. Accession No. A0R5M7.1. Fleishmann et al., Jun 24, 2015. 4 pages.
Seebeck, In Vitro Reconstitution of Mycobacterial Ergothioneine Biosynthesis. J Am Chem Soc. Apr. 26, 2010;132(19):6632-3. Supporting Information. S1-14.
Genghof et al., Biosynthesis of Ergothioneine and Hercynine by Mycobacteria. J Bacteriol. Apr. 1964;87:852-62.
Melville et al., Ergothioneine in microorganisms. J Biol Chem. Nov. 1956;223(1):9-17.
Heath et al., The biosynthesis of ergothioneine and histidine by Claviceps purpurea. I. The incorporation of [2-14C]acetate. Biochem J. Dec. 1956;64(4):612-20.
Hu et al., Bioinformatic and biochemical characterizations of C-S bond formation and cleavage enzymes in the fungus Neurospora crassa ergothioneine biosynthetic pathway. Org Lett. Oct. 17, 2014;16(20):5382-5. doi: 10.1021/ol502596z. Epub Oct. 2, 2014.
Khonde et al., Improved synthesis of the super antioxidant, ergothioneine, and its biosynthetic pathway intermediates. Org Biomol Chem. Feb. 7, 2015;13(5):1415-9. doi: 10.1039/c4ob02023e.
Mashabela et al., Substrate specificity of an oxygen dependent sulfoxide synthase in ovothiol biosynthesis. Chem Commun (Camb). Sep. 11, 2013;49(70):7714-6. doi: 10.1039/c3cc42594k.

(Continued)

*Primary Examiner* — Delia M Ramirez
(74) *Attorney, Agent, or Firm* — Wolf, Greenfield & Sacks, P.C.; Karen K. Chan

(57) ABSTRACT

Disclosed are methods for ergothioneine biosynthesis. More particularly, the present disclosure relates to methods for microbial ergothioneine biosynthesis. The present disclosure relates generally to engineered host cells and methods for producing ergothioneine. More particularly, the present disclosure relates to an engineered host cell and methods for microbial ergothioneine biosynthesis using the engineered host cell.

16 Claims, 9 Drawing Sheets
Specification includes a Sequence Listing.

(56) References Cited

OTHER PUBLICATIONS

Pfeiffer et al., Cyanobacteria produce high levels of ergothioneine. Food Chem. 2011;129:1766-1769.
Seebeck, In vitro reconstitution of Mycobacterial ergothioneine biosynthesis. J Am Chem Soc. May 19, 2010;132(19):6632-3. Supporting Information only.
PCT/US2015/027977, Aug. 12, 2015, International Search Report and Written Opinion.
PCT/US2015/027977, May 3, 2016, International Preliminary Report on Patentability.
Heath et al., 2-Mercaptoglyoxalines. Part I. The Synthesis of Ergothioneine. J Chem Soc. 1951. 2215-2217.
Database UNIPARC [Online] Aug. 5, 2012 (Sep. 5, 2012), "AFP42516—*Mycobacterium smegmatis* str. MC2 155 Aminotransferase class V", Database accession No. UPI000274B31B.
Jones et al., The evolutionary history of the genes involved in the biosynthesis of the antioxidant ergothioneine. Gene. Oct. 1, 2014;549(1):161-70. doi: 10.1016/j.gene.2014.07.065. Epub Jul. 26, 2014.
Pluskal et al., Genetic and metabolomic dissection of the ergothioneine and selenoneine biosynthetic pathway in the fission yeast, S. pombe, and construction of an overproduction system. PLoS One. May 14, 2014;9(5):e97774. doi: 10.1371/journal.pone.0097774. eCollection 2014.

\* cited by examiner

MICROBIAL ERGOTHIONEINE BIOSYNTHESIS

RELATED APPLICATIONS

This application is a National Stage Application under 35 U.S.C. § 371 of International PCT Application No. PCT/US2015/027977, filed Apr. 28, 2015, and entitled "MICROBIAL ERGOTHIONEINE BIOSYNTHESIS", which claims the benefit under 35 U.S.C. § 119(e) of U.S. Provisional Application Ser. No. U.S. 61/985,778, entitled "MICROBIAL ERGOTHIONEINE BIOSYNTHESIS," filed on Apr. 29, 2014, the contents of each of which are herein incorporated by reference in their entirety.

STATEMENT IN SUPPORT FOR FILING A SEQUENCE LISTING

A computer readable form of the Sequence Listing, a text file named "C149770015U501-SEQLIST-AM.txt", which is 19,541 bytes in size (as measured in MICROSOFT WINDOWS® EXPLORER), is filed concurrently herewith via EFS-Web and is herein incorporated by reference. This Sequence Listing consists of SEQ ID NOs:1-16.

BACKGROUND OF THE DISCLOSURE

The present disclosure relates generally to methods for ergothioneine biosynthesis. More particularly, the present disclosure relates to methods for microbial ergothioneine biosynthesis.

Ergothioneine (ET) is a histidine betaine derivative with a thiol group attached to the $C_2$ atom of the imidazole ring. As a thione tautomer, ET is a very stable antioxidant with unique properties. Unlike glutathione and ascorbate, ET can scavenge oxidizing species that are not free radicals. ET is a natural compound that is produced in Actinobacteria such as *Mycobacterium smegmatis* and filamentous fungi such as *Neurospora crassa*. Other species of bacteria, such as *Bacillus subtilis, Escherichia coli, Proteus vulgaris* and *Streptococcus*, as well as fungi belonging to the groups Ascomycetes and Deuteromycetes, cannot make ergothioneine. Animals and plants also cannot make ergothioneine and must obtain it from dietary sources or in the case of plants, from their environment.

Although the function of ET in microbial cells is not well understood, it is believed to be critical in human physiology. Humans absorb ET from dietary sources and ET accumulates in specific tissues and cells such as the liver, kidney, central nervous system, and red blood cells. It is evidenced that a specific cation transporter (OCTN1) has high affinity for ET in the human body, and both hyperactivity and deficiency of the transporter exert negative effects on human cells.

The biosynthesis of ET has been detected in certain mycobacteria fungi, however, the exact metabolic pathway is not completed or only partially confirmed. Seebeck reconstituted mycobacterial ergothioneine biosynthesis in vitro using *E. coli* to separately express a formylglycine-generating enzyme-like protein (EgtB), a glutamine amidotransferase (EgtC), a histidine methyltransferase (EgtD), and an unrelated β-lyase from *Erwinia tasmaniensis* to replace the pyridoxal 5-phosphate binding protein (EgtE), because the recombinant production of soluble EgtE protein failed (see, J. Am. Chem. Soc. 2010, 132:6632-6633).

Thus far, only 3 genes coding for EgtB, EgtC, and EgtD have been identified for the production of ergothioneine in vitro. A putative gene for EgtE remains uncharacterized either in vitro or in vivo. To date, no microbial production using the above genes to engineer the mycobacterial ergothioneine metabolic pathway in *E. coli* has been reported despite various attempts at bio-conversion. Also, although various fungal and mycobacterial sources are available for the ergothioneine extraction, the yields are too low to be commercially viable for industrial production of ergothioneine. Accordingly, there exists a need for producing ergothioneine.

SUMMARY OF THE DISCLOSURE

The present disclosure relates generally to engineered host cells and methods for producing ergothioneine. More particularly, the present disclosure relates to an engineered host cell and methods for microbial ergothioneine biosynthesis using the engineered host cell.

In one aspect, the present disclosure is directed to a transformed host cell for producing ergothioneine comprising a nucleic acid sequence encoding EgtB, a nucleic acid sequence encoding EgtC, a nucleic acid sequence encoding EgtD and a nucleic acid sequence encoding EgtE.

In another aspect, the present disclosure is directed to a method for producing ergothioneine. The method comprises culturing a host cell, wherein the host cell is transformed with a nucleic acid sequence encoding EgtB, a nucleic acid sequence encoding EgtC, a nucleic acid sequence encoding EgtD and a nucleic acid sequence encoding EgtE; inducing the host cell to express the nucleic acid sequence encoding EgtB, the nucleic acid sequence encoding EgtC, the nucleic acid sequence encoding EgtD and the nucleic acid sequence encoding EgtE; and collecting the ergothioneine.

In another aspect, the present disclosure is directed to an expression vector for the production of ergothioneine, comprising a nucleic acid sequence encoding an amino acid sequence selected from the group consisting of EgtB, EgtC, EgtD and EgtE.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1A:
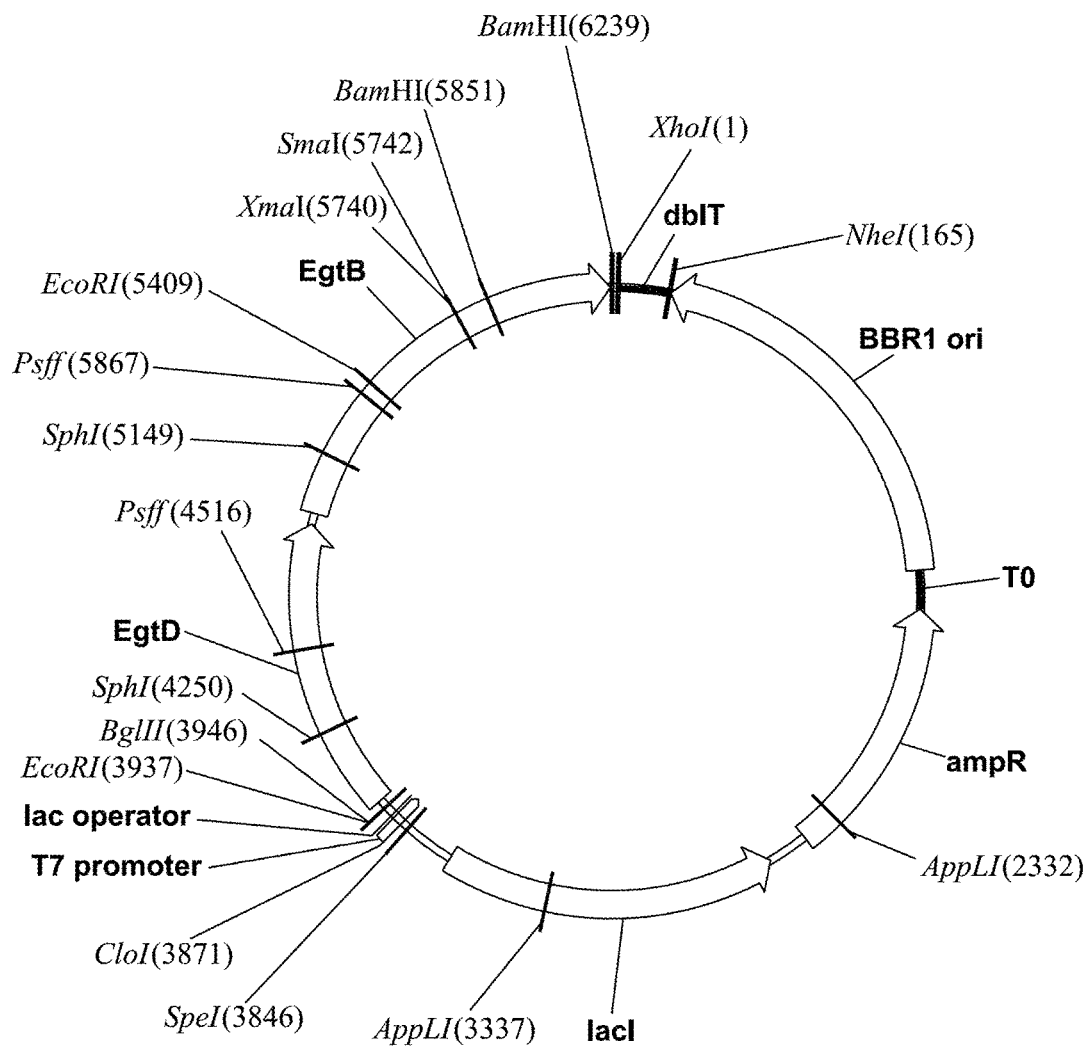
FIG. 1A is a vector map containing the EgtD and EgtB genes, as discussed in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

The term "complementary" is used according to its ordinary and customary meaning as understood by a person of ordinary skill in the art, and is used without limitation to describe the relationship between nucleotide bases that are capable to hybridizing to one another. For example, with respect to DNA, adenosine is complementary to thymine, and cytosine is complementary to guanine. Accordingly, the subjection technology also includes isolated nucleic acid fragments that are complementary to the complete sequences as reported in the accompanying Sequence Listing as well as those substantially similar nucleic acid sequences.

The terms "nucleic acid" and "nucleotide" are used according to their respective ordinary and customary meanings as understood by a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is used according to its ordinary and customary meaning as understood by a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein refers to a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are used according to their respective ordinary and customary meanings as understood by a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are used according to their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from superfamilies and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical.

"Percent (%) amino acid sequence identity" with respect to the variant polypeptide sequences of the subject technology refers to the percentage of amino acid residues in a candidate sequence that are identical with the amino acid residues of a reference polypeptide (such as, for example, SEQ ID NO:6), after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

"Coding sequence" is used according to its ordinary and customary meaning as understood by a person of ordinary skill in the art, and is used without limitation to refer to a DNA sequence that encodes for a specific amino acid sequence.

"Suitable regulatory sequences" is used according to its ordinary and customary meaning as understood by a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is used according to its ordinary and customary meaning as understood by a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different cell types, or at different stages of development, or in response to different environmental conditions. Promoters that cause a gene to be expressed in most cell types at most times are commonly referred to as "constitutive promoters." It is further recognized that since, in most cases, the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is used according to its ordinary and customary meaning as understood by a person of ordinary skill in the art, and is used without limitation to refer to the transcription and stable accumulation of sense (mRNA) or antisense RNA derived from the nucleic acid fragment of the subject technology. "Overexpression" refers to the production of a gene product in transgenic or recombinant organisms that exceeds levels of production in normal or non-transformed organisms.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are used according to their ordinary and customary meanings as understood by a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are used according to their ordinary and customary meanings as understood by a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described, for example, by Sambrook, J., Fritsch, E. F. and Maniatis, T. Molecular Cloning: A Laboratory Manual, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; the entireties of each of which are hereby incorporated herein by reference to the extent they are consistent herewith.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, methods have been developed for producing ergothioneine and host cells having genes encoding EgtB, EgtC, EgtD and EgtE that are useful for producing ergothioneine. Surprisingly and unexpectedly, an ergothioneine production pathway has been reproduced in an in vitro microbial production system.

Engineered Host Cell for Producing Ergothioneine

In one aspect, the present disclosure is directed to an engineered host cell. The engineered host cell includes a nucleic acid sequence encoding EgtB, a nucleic acid sequence encoding EgtC, a nucleic acid sequence encoding EgtD and a nucleic acid sequence encoding EgtE.

EgtB (or iron(II)-dependent oxidoreductase EgtB) catalyzes the oxidative sulfurization of hercynine via the addition of oxygen and gamma-glutamyl-cysteine on hercynine (N-alpha,N-alpha,N-alpha-trimethyl-L-histidine).

A suitable EgtB can be, for example, *Mycobacterium* EgtB. A particularly suitable EgtB can be, for example, an EgtB nucleic acid sequence encoding an amino acid sequence at least 95% identical to the amino acid sequence provided in SEQ ID NO:2. In another aspect, a particularly suitable EgtB can be, for example, an EgtB nucleic acid sequence encoding an amino acid sequence at least 96% identical to the amino acid sequence provided in SEQ ID NO:2. In another aspect, a particularly suitable EgtB can be, for example, an EgtB nucleic acid sequence encoding an amino acid sequence at least 97% identical to the amino acid sequence provided in SEQ ID NO:2. In another aspect, a particularly suitable EgtB can be, for example, an EgtB nucleic acid sequence encoding an amino acid sequence at least 98% identical to the amino acid sequence provided in SEQ ID NO:2. In another aspect, a particularly suitable EgtB can be, for example, an EgtB nucleic acid sequence encoding an amino acid sequence at least 99% identical to the amino acid sequence provided in SEQ ID NO:2. In another aspect, a particularly suitable EgtB can be, for example, an EgtB nucleic acid sequence encoding an amino acid sequence 100% identical to the amino acid sequence provided in SEQ ID NO:2.

EgtC (or Amidohydrolase EgtC) catalyzes the hydrolysis of the gamma-glutamyl amide bond from N-(gamma-glutamyl)-[N(alpha),N(alpha),N(alpha)-trimethyl-L-histidinyl]-cysteine sulfoxide to produce hercynylcysteine sulfoxide.

A suitable EgtC can be, for example, *Mycobacterium* EgtC. A particularly suitable EgtC can be, for example, an EgtC nucleic acid sequence encoding an amino acid sequence at least 95% identical to the amino acid sequence provided in SEQ ID NO:4. In another aspect, a particularly suitable EgtC can be, for example, an EgtC nucleic acid sequence encoding an amino acid sequence at least 96% identical to the amino acid sequence provided in SEQ ID NO:4. In another aspect, a particularly suitable EgtC can be, for example, an EgtC nucleic acid sequence encoding an amino acid sequence at least 97% identical to the amino acid sequence provided in SEQ ID NO:4. In another aspect, a particularly suitable EgtC can be, for example, an EgtC nucleic acid sequence encoding an amino acid sequence at least 98% identical to the amino acid sequence provided in SEQ ID NO:4. In another aspect, a particularly suitable EgtC can be, for example, an EgtC nucleic acid sequence encoding an amino acid sequence at least 99% identical to the amino acid sequence provided in SEQ ID NO:4. In another aspect, a particularly suitable EgtC can be, for example, an EgtC nucleic acid sequence encoding an amino acid sequence 100% identical to the amino acid sequence provided in SEQ ID NO:4.

EgtD (or histidine-specific methyltransferase EgtD) catalyzes the methylations of histidine to form N-alpha,N-alpha,N-alpha-trimethyl-L-histidine (also known as hercynine). Histidine and alpha-N,N-dimethylhistidine are preferred substrates.

A suitable EgtD can be, for example, *Mycobacterium* EgtD. A particularly suitable EgtD can be, for example, an EgtD nucleic acid sequence encoding an amino acid sequence at least 95% identical to the amino acid sequence provided in SEQ ID NO:6. In another aspect, a particularly suitable EgtD can be, for example, an EgtD nucleic acid sequence encoding an amino acid sequence at least 96% identical to the amino acid sequence provided in SEQ ID NO:6. In another aspect, a particularly suitable EgtD can be, for example, an EgtD nucleic acid sequence encoding an amino acid sequence at least 97% identical to the amino acid sequence provided in SEQ ID NO:6. In another aspect, a particularly suitable EgtD can be, for example, an EgtD nucleic acid sequence encoding an amino acid sequence at least 98% identical to the amino acid sequence provided in SEQ ID NO:6. In another aspect, a particularly suitable EgtD can be, for example, an EgtD nucleic acid sequence encoding an amino acid sequence at least 99% identical to the amino acid sequence provided in SEQ ID NO:6. In another aspect, a particularly suitable EgtD can be, for example, an EgtD nucleic acid sequence encoding an amino acid sequence 100% identical to the amino acid sequence provided in SEQ ID NO:6.

EgtE (or pyridoxal-phosphate-dependent protein EgtE) is believed to catalyze the removing of pyruvate, ammonia and oxygen to produce ergothioneine.

A suitable EgtE can be, for example, *Mycobacterium* EgtE. A particularly suitable EgtE can be, for example, an EgtE nucleic acid sequence encoding an amino acid sequence at least 95% identical to the amino acid sequence provided in SEQ ID NO:8. In another aspect, a particularly suitable EgtE can be, for example, an EgtE nucleic acid sequence encoding an amino acid sequence at least 96% identical to the amino acid sequence provided in SEQ ID NO:8. In another aspect, a particularly suitable EgtE can be, for example, an EgtE nucleic acid sequence encoding an amino acid sequence at least 97% identical to the amino acid sequence provided in SEQ ID NO:8. In another aspect, a particularly suitable EgtE can be, for example, an EgtE nucleic acid sequence encoding an amino acid sequence at least 98% identical to the amino acid sequence provided in SEQ ID NO:8. In another aspect, a particularly suitable EgtE can be, for example, an EgtE nucleic acid sequence encoding an amino acid sequence at least 99% identical to the amino acid sequence provided in SEQ ID NO:8. In another aspect, a particularly suitable EgtE can be, for example, an EgtE nucleic acid sequence encoding an amino acid sequence 100% identical to the amino acid sequence provided in SEQ ID NO:8.

Suitable host cells can be, for example, bacterial cells and yeast cells. Suitable bacterial cells can be, for example, *Escherichia coli*.

Suitable yeast cells can be, for example, *Saccharomyces* and *Pichia*. Particularly suitable *Saccharomyces* can be, for example, *Saccharomyces cerevisiae*. Particularly suitable *Pichia* can be, for example, *Pichia pastoris*.

The nucleic acid sequences encoding EgtB, EgtC, EgtD and EgtE are cloned into an expression vector under the control of a promoter known by those skilled in the art. Suitable promoters can be, for example, constitutively active promoters and inducible promoters known by those skilled in the art. Suitable inducible promoters are known by those skilled in the art and can be, for example, chemical inducers, nutrient addition, nutrient depletion and physical or physiochemical factor shift such as, for example a pH shift and temperature-induction. Suitable chemical inducers can be, for example, an isopropyl β-D-1-thiogalactopyranoside (IPTG)-inducible promoter and antibiotic-inducible promoters known by those skilled in the art. A particularly suitable chemically-inducible promoter can be, for example, an isopropyl β-D-1-thiogalactopyranoside (IPTG)-inducible promoter known by those skilled in the art. Other suitable inducible promoters can be, for example, a temperature-induced promoter known by those skilled in the art such as, for example, pL and pR λ, phage promoters.

Figure 1B:
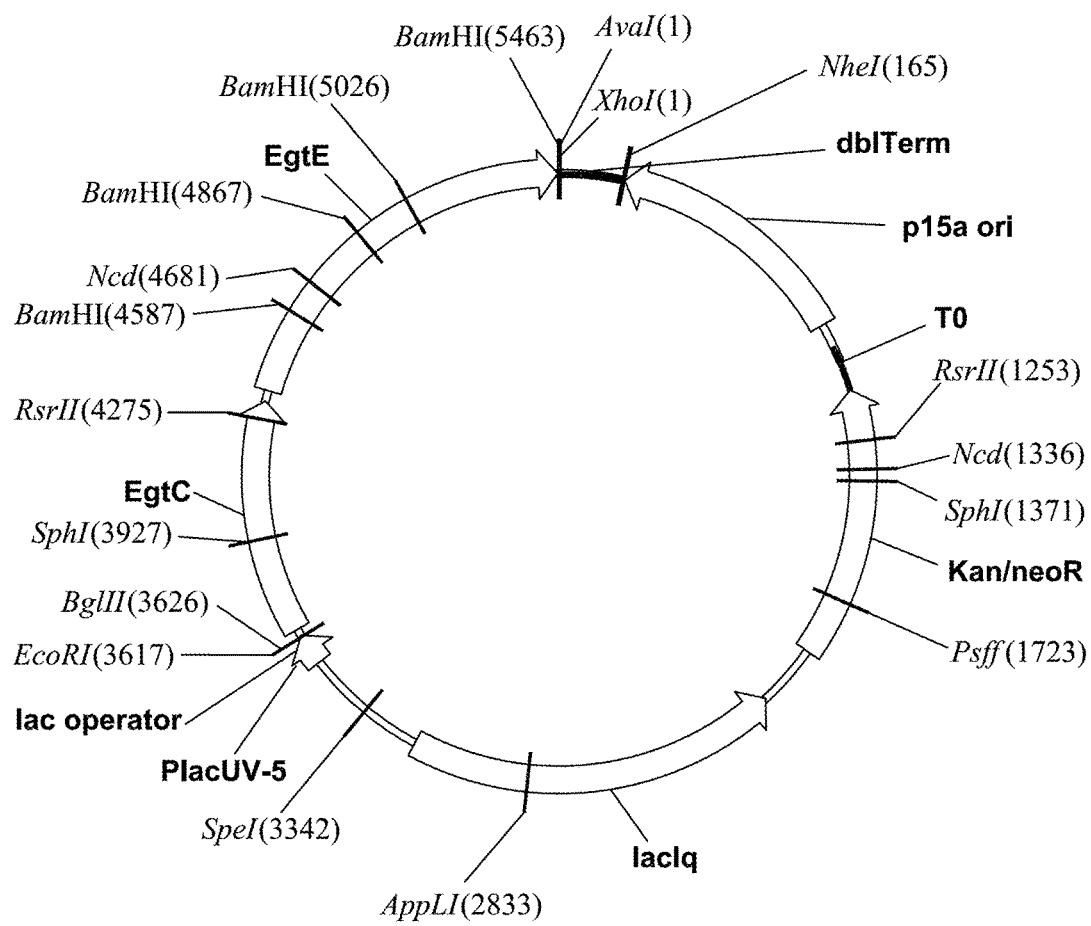
FIG. 1B is a vector map containing the EgtC and EgtE genes, as discussed in Example 1.

Particularly suitable expression vectors are illustrated in FIGS. 1A and 1B. Other suitable expression vectors are known to those in the art and can be, for example, pET vectors, pCDF vectors, pRSF vectors and Duet vectors.

Methods for Producing Ergothioneine

In another aspect, the present disclosure is directed to a method for producing ergothioneine. The method includes culturing an host cell, wherein the host cell is transformed with a nucleic acid sequence encoding EgtB, a nucleic acid sequence encoding EgtC, a nucleic acid sequence encoding EgtD and a nucleic acid sequence encoding EgtE; inducing the host cell to express the nucleic acid sequence encoding EgtB, the nucleic acid sequence encoding EgtC, the nucleic acid sequence encoding EgtD and the nucleic acid sequence encoding EgtE; and collecting the ergothioneine.

The method can further include adding a substrate to the culture. Suitable amounts of substrates can be, for example, from about 1 mM to about 20 mM. Particularly suitable substrates can be, for example, histidine, methionine, cysteine, γ-glutamyl cysteine and combinations thereof.

In another embodiment, the method can include adding a cofactor to the culture. Suitable amounts of cofactors can be, for example, from about 0.05 mM to about 0.4 mM. A particularly suitable cofactor can be, for example iron (II) ($Fe^{++}$).

Suitable host cells can be, for example, bacterial cells and yeast cells. Suitable bacterial cells can be, for example, *Escherichia coli*.

Suitable yeast cells can be, for example, *Saccharomyces* and *Pichia*. Particularly suitable *Saccharomyces* can be, for example, *Saccharomyces cerevisiae*. Particularly suitable *Pichia* can be, for example, *Pichia pastoris*.

In one embodiment, the host cell can produce from about 10 milligrams to about 30 milligrams of ergothioneine per liter.

The disclosure will be more fully understood upon consideration of the following non-limiting Examples.

EXAMPLES

Example 1

In this Example, nucleic acid sequences for EgtB, EgtC, EgtD and EgtE were cloned into *E. coli*.

Specifically, the following sequences were obtained from GenBank (accession number NC 008596): Egt B: MSMEG_6249 (SEQ ID NO:1); Egt C: MSMEG_6248 (SEQ ID NO:3); Egt D: MSMEG_6247 (SEQ ID NO:5); and Egt E: MSMEG_6246 (SEQ ID NO:7). The genes were introduced into a vector under control of an IPTG-inducible promoter.

To build the ET pathway in *E. coli*, the EgtB, C, D, E nucleic acid sequences were PCR-amplified from the genomic sequence of *M. smegmatis* using the primer pairs summarized in Table 1. All of the 5'-primers used for cloning included EcoRI and BglI restriction sites and a ribosomal binding site (RBS) and all of the 3'-primers included BamHI-XhoI sites. The EgtD and EgtB sequences were cloned into a pConB7A vector (FIG. 1A) and the EgtC and EgtE sequences were cloned into a pConA5K vector (FIG. 1B). No sequence errors were identified in the cloned sequences. The empty vectors were prepared in the same manner. The constructs were then co-transformed into *E. coli* strain BL21(DE3).

TABLE 1

Primers for gene cloning.

| Primer | Sequence | SEQ ID NO |
|---|---|---|
| EgtB-5' | AGAATTCAAAAGATCTAAAGGAGGCCATCCATGATC GCACGCGAGACAC | 9 |
| EgtB-3' | ACTCGAGTTTGGATCCTCAGACGTCCCAGGCCAGGC GGACACCCGAGAATATC | 10 |
| EgtC-5' | AGAATTCAAAAGATCTAAAGGAGGCCATCCATGTGC CGGCATGTGGCGTG | 11 |
| EgtC-3' | ACTCGAGTTTGGATCCTCACAGGGGTGTCACGAC | 12 |
| EgtD-5' | AGAATTCAAAAGATCTAAAGGAGGCCATCCATGACG CTCTCACTGGCCAAC | 13 |
| EgtD-3' | ACTCGAGTTTGGATCCTCACCGCACCGCCAGCGAC | 14 |
| EgtE-5' | AGAATTCAAAAGATCTAAAGGAGGCCATCCATGCTC GCGCAGCAGTG | 15 |
| EgtE-3' | ACTCGAGTTTGGATCCTCAGGGCGCCTCACGCAAC | 16 |

Example 2

In this Example, ergothioneine was produced in an engineered microbial system.

Specifically, *E. coli* were transformed with the pConB7A vector and the pConA5K vectors encoding EgtB, EgtC, EgtD and EgtE as described in Example 1. To co-express the four genes (EgtB, C, D, E) in *E. coli* system, the transformants were grown in the LB media containing 100 mg/L ampicillin and 50 mg/L kanamycin at 37° C. until reaching an $OD_{600}$~0.6. Expression was induced by the addition of 0.2-0.5 mM of isopropyl β-D-1-thiogalactopyranoside (IPTG) and the culture was further grown at either 30° C. or 37° C. for 16-24 hours. Cells were harvested by centrifugation and the supernatant and cell pellet were collected separately. The supernatant was centrifuged at 16,000×g for 5 min for HPLC analysis. The pellet was resuspended in 1 ml of 50% methanol and sonicated for 1 minute (3×20 sec). After centrifuging at 16,000×g for 5 minutes, a 5 µl of sample was analyzed by HPLC, as described below. *E. coli* that were transformed with the empty vector were treated in the same manner and analyzed by HPLC. A sample obtained from IPTG-induced *E. coli* containing the EgtB, EgtC, EgtD, EgtE genes was spiked with 20 mg/L ergothioneine and analyzed by HPLC.

Samples were analyzed using a Dionex UPLC Ultimate 3000 (Sunnyvale, Calif.). The compounds were separated on an Atlantis HILIC Silica column (particle size 3.0 lam, diameter×length=2.1×100 mm; Waters) and detected at 264 nm. The mobile phase consisted of 0.1% formic acid in water (A) and 0.1% formic acid in acetonitrile (B). The program of a gradient was 95% B at 1 min, 40% B at 8 minutes, 95% B at 8.1 minutes, stop at 11 min. The flow rate was 0.6 ml/minute and the inject volume was 5 µl.

Figure 2:
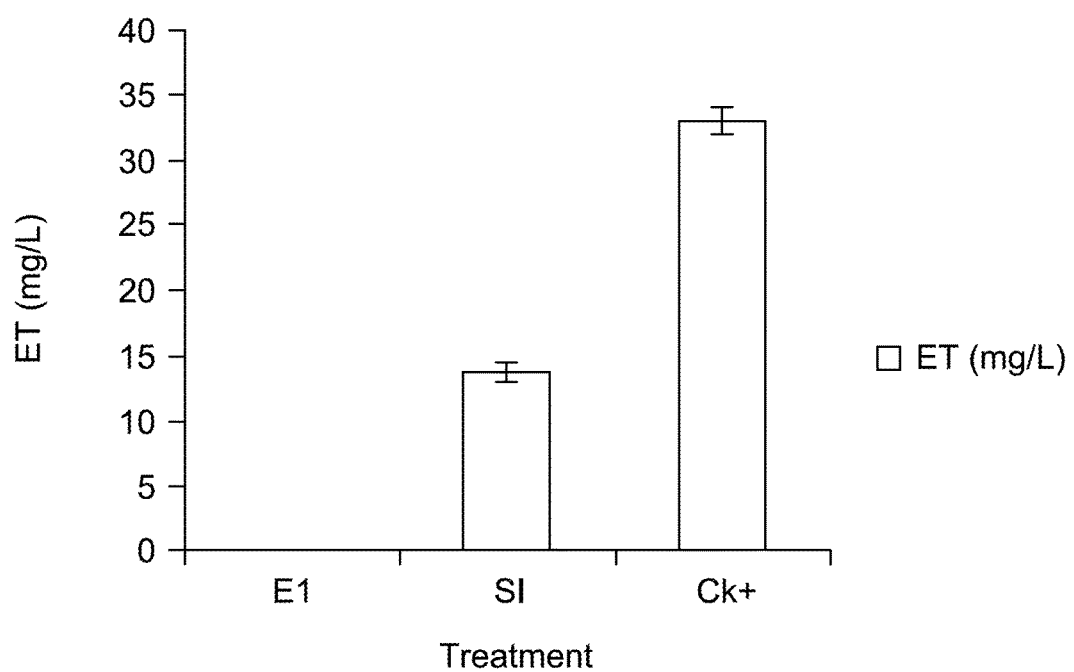
FIG. 2 is a graph illustrating the production of ET only in the strain containing all four genes, as discussed in Example 2. EI, empty vector cells induced with IPTG; SI, strain containing the four genes induced with IPTG; Ck+, the sample with the addition of 20 mg/L ergothioneine.

As shown in FIG. 2, ET surprisingly accumulated only in the IPTG-induced *E. coli* strain containing the EgtB, EgtC, EgtD, EgtE sequences ("SI"), successfully demonstrating biosynthesis of ET in engineered *E. coli*. In contrast, the IPTG-induced *E. coli* containing the empty vector did not produce any ET ("EI"). In the ET-spiked sample, the ET peak from the IPTG-induced *E. coli* strain containing the EgtB, EgtC, EgtD and EgtE overlapped with the added ergothioneine and demonstrated an increased level to account for the added ET ("Ck+").

Figure 3A:
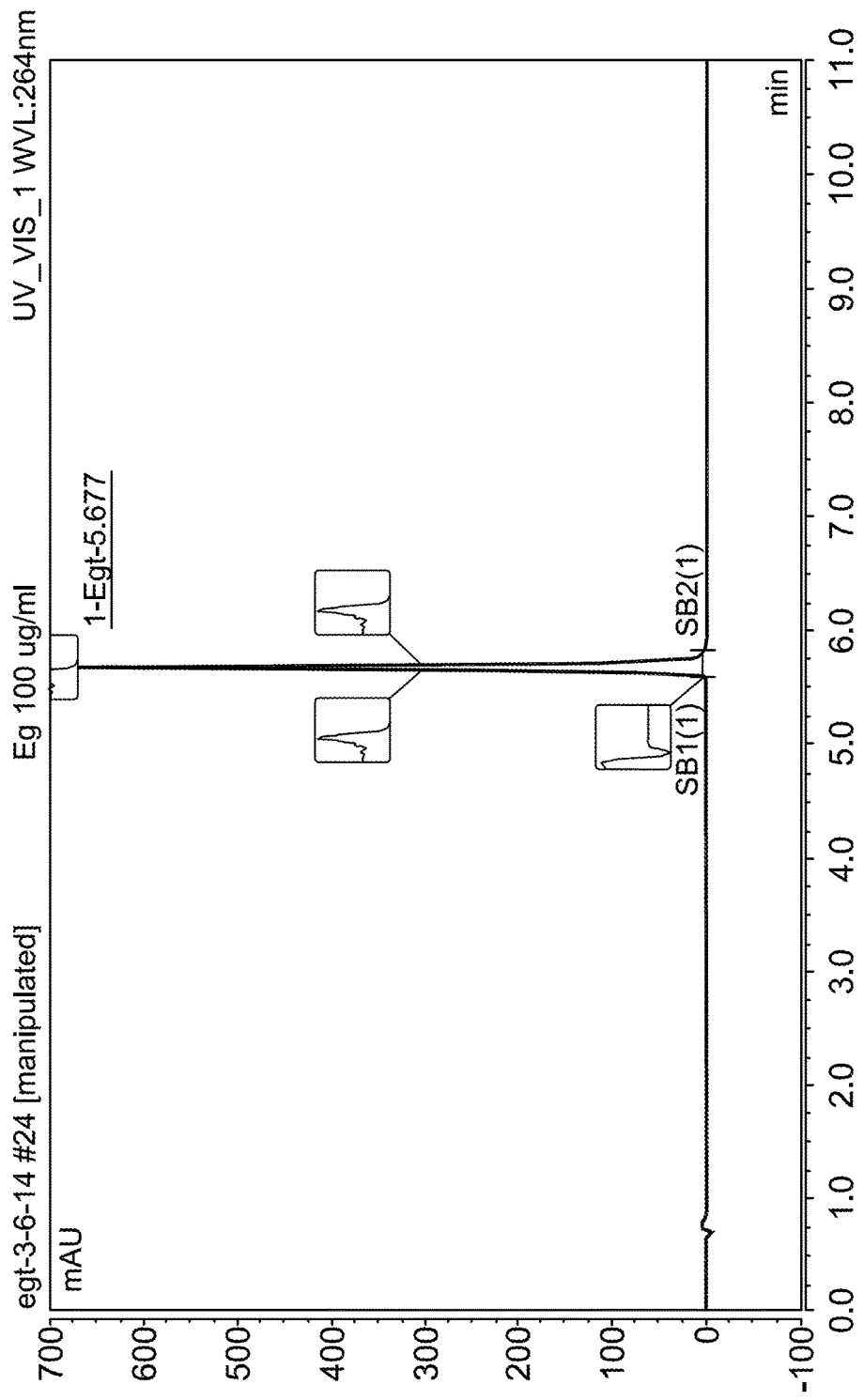
FIGS. 3A and 3B are graphs showing the HPLC retention time and UV-spectrum of a 100 mg/L ergothioneine standard, as discussed in Example 2.
Figure 3B:
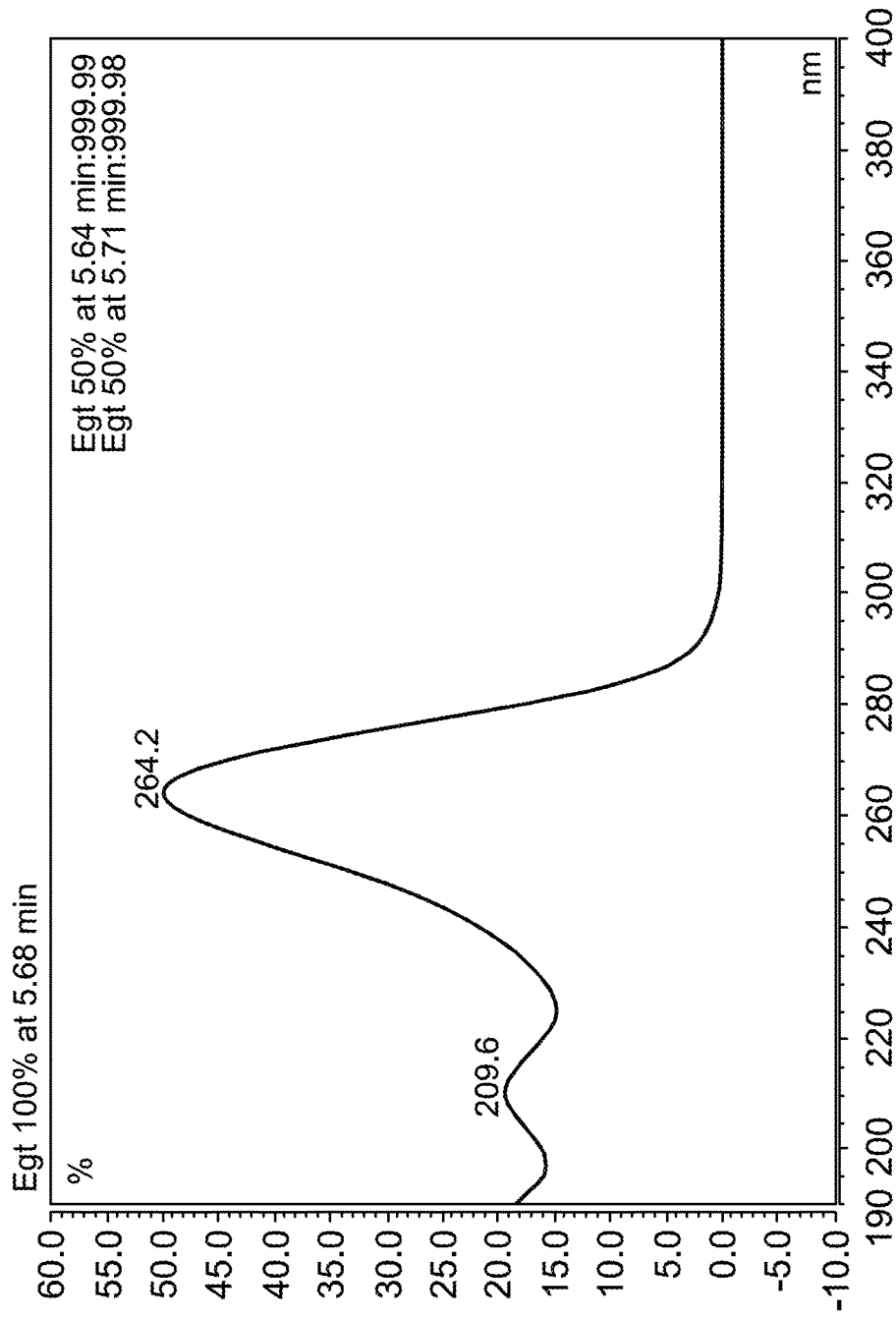
Figure 4A:
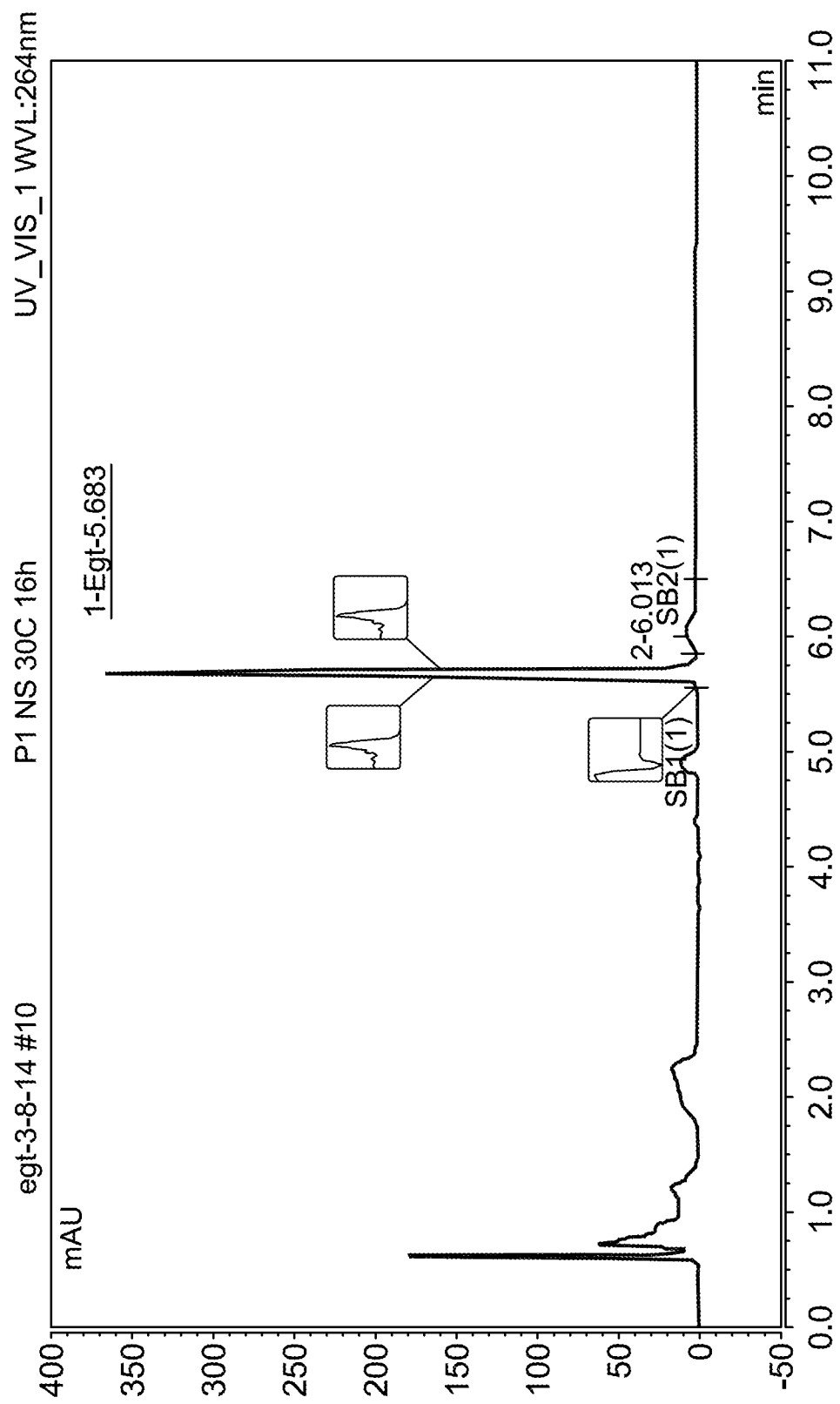
FIGS. 4A and 4B are graphs showing the HPLC retention time and UV-spectrum of ergothioneine produced in *E. coli* transformed with nucleic acid sequences encoding EgtB, EgtC, EgtD and EgtE, as discussed in Example 2.
Figure 4B:
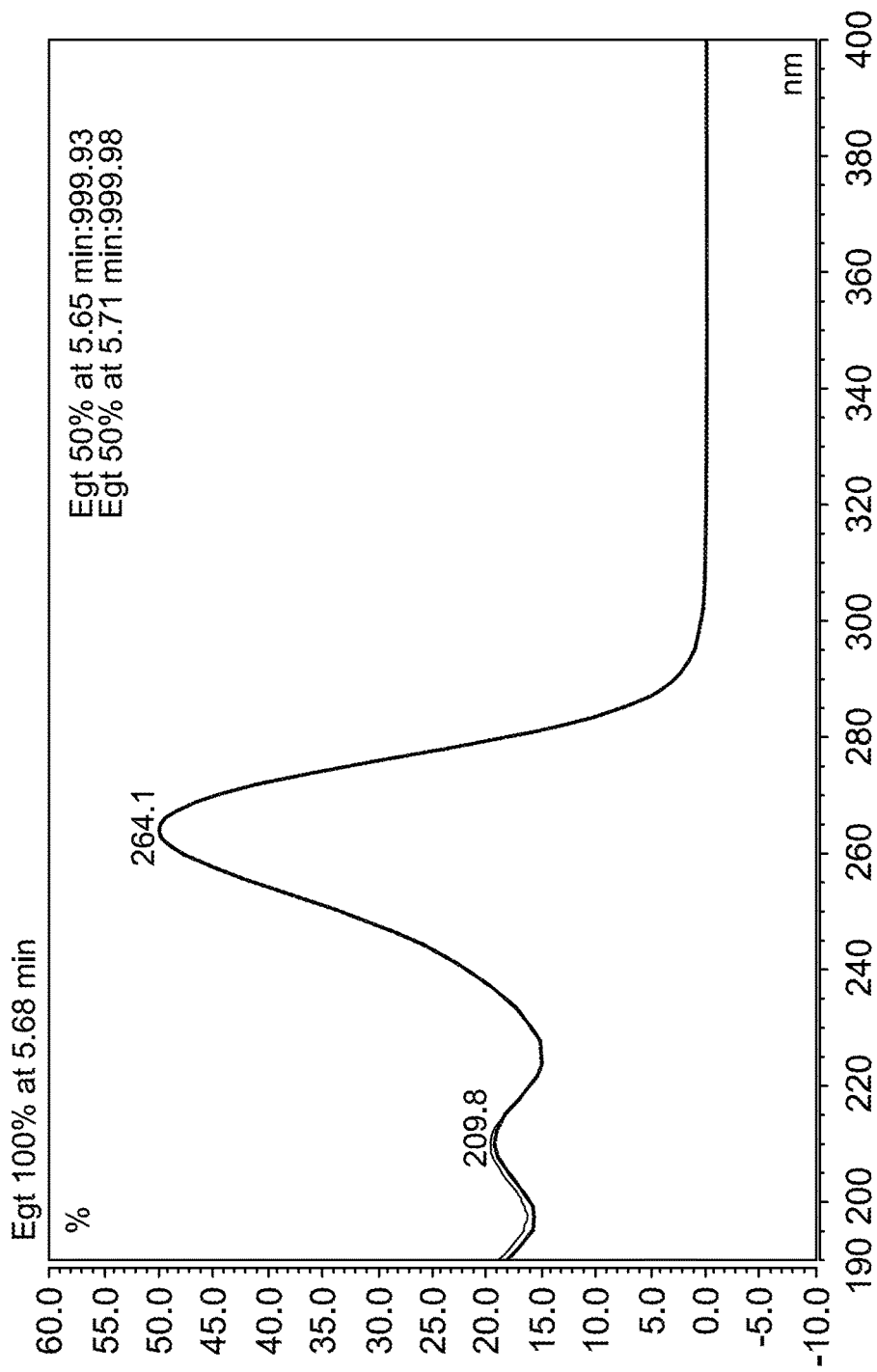

FIGS. 3A and 3B illustrate the HPLC analysis of a 100 mg/L ergothioneine standard. As shown in FIG. 4A, the retention time of the ET from the *E. coli* strain containing EgtB, EgtC, EgtD and EgtE overlapped with the retention time of the ergothioneine standard (see, FIG. 3A). In addition to retention time, the UV-spectrum of the ET peak (see, FIG. 4B) also matched the ergothioneine standard (see, FIG. 3B). These results demonstrated that the peak from the engineered *E. coli* strain expressing the EgtB, EgtC, EgtD and EgtE corresponds to ET.

Example 3

In this Example, a time course for ergothioneine production in an engineered microbial system was performed.

Specifically, *E. coli* were transformed with the vectors containing genes for EgtB, EgtC, EgtD and EgtE as described in Example 1. Control *E. coli* cells included cells with an empty vector (no Egt genes) and a non-induced strain that contained the Egt vectors, but was not induced. Cells were grown at 30° C. or 37° C. as described in Example 2. Samples were taken at different time points from 0 hours to 20 hours. After sonicating for 1 minute (3×20 seconds), the samples were centrifuged at 16,000×g for 5 minutes and a 5 µl sample was analyzed by HPLC as discussed in Example 2.

Figure 5:
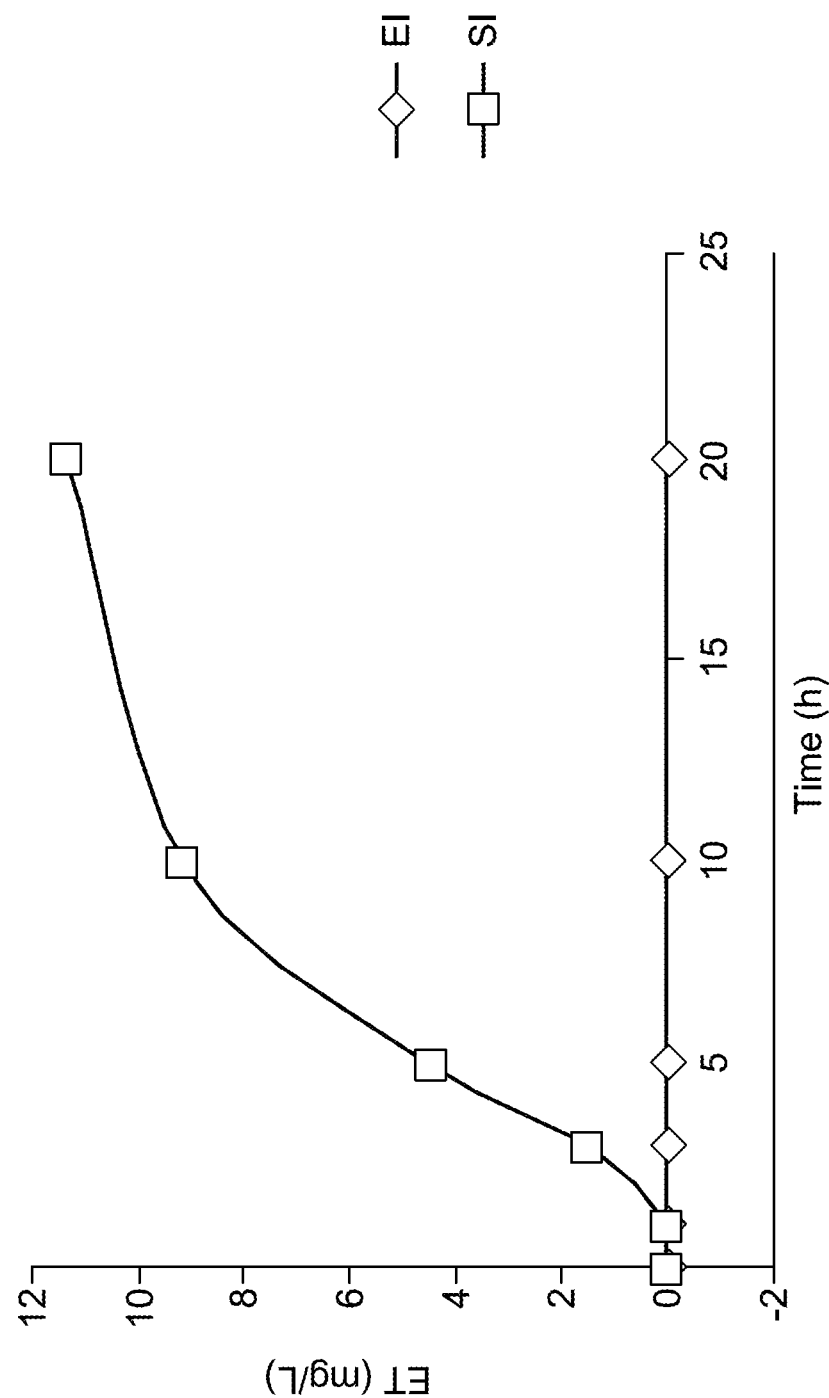
FIG. 5 is a graph showing a time course of ergothioneine production in an engineered *E. coli* cell and empty vector control cell, as discussed in Example 3. EI, empty vector control induced with IPTG; SI, strain containing EgtB, EgtC, EgtD and EgtE induced with IPTG.

As shown in FIG. 5, the HPLC analysis revealed that ET started to be produced by the cells about 1 hour after the IPTG induction. The fastest increase in ET production was observed from about 3 hours up to about 10 hours after the IPTG induction. ET production slowed down after 10 hours, but continued to be produced at least until 20 hours. At the same time, no ET was detected in the empty vector control at all during the entire time course. These results further demonstrated that ET is exclusively produced in the *E. coli* strain engineered to express EgtB, EgtC, EgtD and EgtE.

Example 4

In this Example, feeding experiments were performed to determine the effect on ergothioneine production in the engineered microbial system.

Without being bound by theory, it is believed that ET is synthesized from amino acids such as histidine (His), methionine (Met), and cysteine (Cys). The imidazole ring of ET is supplied by His, which is then methylated to produce histidine betaine. Met is a building block for S-adenosyl methionine (SAM) that serves as a methyl donor. The sulfur atom is incorporated from Cys.

To determine the effect on ergothioneine production in the engineered *E. coli*, several substrates and cofactors such as $Fe^{++}$ were fed to the transgenic *E. coli* cells through the culture media. After 3 hours of induction, 2 mM of His, 4 mM of Met, 4 mM of Cys and 0.2 mM of $Fe^{++}$ were added into media and the cells were further cultured for 16 hours, 24 hours and 42 hours. A control *E. coli* culture (carrying empty vectors) was fed with the same substrates or cofactor. Samples were analyzed by HPLC as discussed in Example 2.

Figure 6:
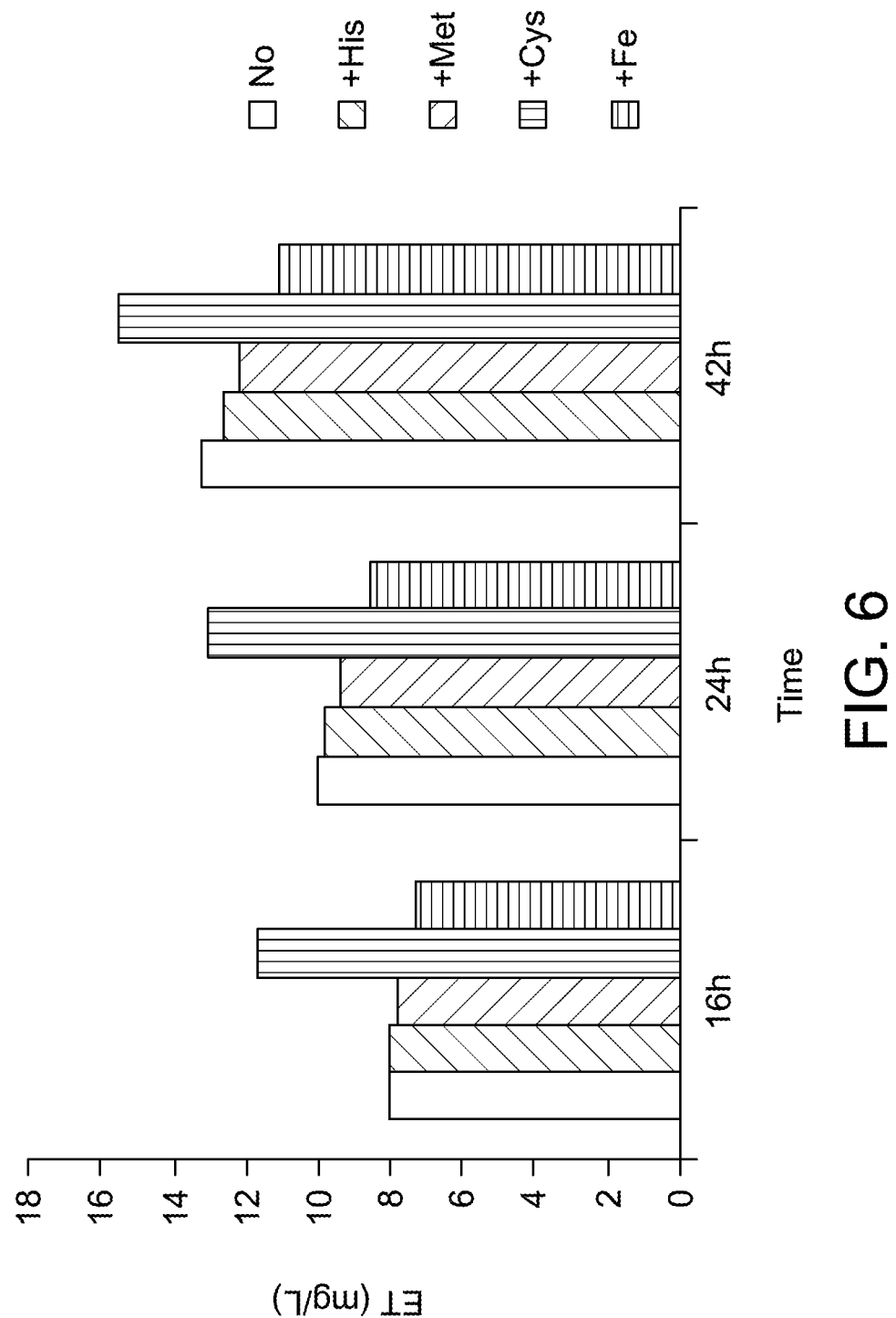
FIG. 6 is a graph showing the transformed *E. coli* strain fed with various substrates and cofactor. No, no added substrates or cofactor; His, histidine; Met, methionine; Cys, cysteine; Fe, iron $Fe^{++}$.

As shown in FIG. 6, the feeding experiments revealed that the addition of Cys increased ET yield by 17.3-44.4% among three time points. This result suggested that Cys and its derivative γ-glutamyl cysteine play an important role in the biosynthesis of ET. The control culture did not produce any ET.

Example 5

In this Example, ergothioneine will be produced in an engineered *S. cerevisiae* yeast system.

To produce the ET in *S. cerevisiae*, the EgtB, C, D, E genes will be cloned into pESC vectors such as pESC-His and pESC-Leu, which are commercially available (Agilent Technologies). These vectors contain the GAL1 and GAL10 yeast promoters in opposing orientation, which allow for the introduction of two genes into a yeast strain under the control of two repressible promoters, respectively. The resulting two constructs will then be co-transformed into *S. cerevisiae*. To co-express the four genes (EgtB, C, D, E) in yeast, the transformants will be grown in media without the two amino acids, histidine and leucine, until reaching an $OD_{600}$~0.4. Expression will be induced by the addition of 2% galactose and the culture will be further grown at either 28° C. or 30° C. for 24-48 hours. Cells will be harvested by centrifuge and the supernatant and cell pellet will be collected separately. The supernatant will be centrifuged at 12,000×g for 5 minutes and analyzed by HPLC. The pellet will be resuspended in 1 ml of 50% methanol and sonicated for 1 min (3×20 sec). After centrifuging at 12,000×g for 5 minutes, 5 µl of sample will be injected to HPLC. Yeast harboring empty vectors will be transformed and analyzed in the same way. The above constructs may be ultimately integrated into the yeast genome and expressed under the control of constitutive promoters such as the GPD promoter or the GAP promoter.

Example 6

In this Example, ergothioneine will be produced in an engineered *P. pastoris* yeast system.

To produce the ET in *P. pastoris*, the EgtB, C, D, E genes will be cloned into pPICZ or pGAPZ vectors, which are commercially available (Invitrogen, Life Technologies). The pPICZ vectors contain the methanol-regulated AOX1 promoter, while pGAPZ vectors have constitutive glyceraldehyde-3-phosphate dehydrogenase (GAP) promoter. The coexpression of the four genes (EgtB, C, D, E) in pPICZ vectors will be induced by 0.5-5% methanol. The production of ET will be analyzed by HPLC analysis using the same method described above.

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An engineered host cell for the production of ergothioneine, wherein the host cell comprises a metabolic pathway for the production of ergothioneine, wherein the host cell is *Escherichia coli*, *Saccharomyces cerevisiae*, or *Pichia pastoris*, and wherein the host cell comprises:
   a heterologous oxidoreductase (EgtB) comprising an amino acid sequence having at least 99% sequence identity to SEQ ID NO: 2,
   a heterologous amidohydrolase (EgtC) comprising an amino acid sequence having at least 99% sequence identity to SEQ ID NO: 4,
   a heterologous histidine methyltransferase (EgtD) comprising an amino acid sequence having at least 99% sequence identity to SEQ ID NO: 6, and
   a heterologous pyridoxal 5-phosphate binding protein (EgtE) comprising an amino acid sequence having at least 99% sequence identity to SEQ ID NO: 8,
   wherein EgtB, EgtC, EgtD, and EgtE and up to two selectable markers are the only heterologous enzymes in the host cell.

2. The engineered host cell of claim 1, wherein the heterologous EgtB comprises the amino acid sequence of SEQ ID NO:2.

3. The engineered host cell of claim 1, wherein the heterologous EgtC comprises the amino acid sequence of SEQ ID NO:4.

4. The engineered host cell of claim 1, wherein the heterologous EgtD comprises the amino acid sequence of SEQ ID NO:6.

5. The engineered host cell of claim 1, wherein the heterologous EgtE comprises the amino acid sequence of SEQ ID NO:8.

6. The engineered host cell of claim 1, wherein the heterologous EgtB comprises the amino acid sequence of SEQ ID NO:2, the heterologous EgtC comprises the amino acid sequence of SEQ ID NO:4, the heterologous EgtD comprises the amino acid sequence of SEQ ID NO:6, and the heterologous EgtE comprises the amino acid sequence of SEQ ID NO:8.

7. The engineered host cell of claim 1, wherein the host cell is an *E. coli* cell.

8. The engineered host cell of claim 1, wherein the host cell is a *Saccharomyces cerevisiae* cell.

9. The engineered host cell of claim 1, wherein the host cell is a *Pichia pastoris* cell.

10. A method for producing ergothioneine, the method comprising:
    culturing the host cell of claim 1,
    inducing the host cell to express the heterologous EgtB, the heterologous EgtC, the heterologous EgtD and the heterologous EgtE; and
    collecting the ergothioneine.

11. The method of claim 10, wherein a substrate selected from the group consisting of histidine, methionine, cysteine, γ-glutamyl cysteine and combinations thereof is added to the culture.

12. The method of claim 10, wherein iron (II) is added to the culture.

13. The method of claim 10, wherein the host cell is an *E. coli* cell.

14. The method of claim 10, wherein the host cell is a *Saccharomyces cerevisiae* cell.

15. The method of claim 10, wherein the host cell is a *Pichia pastoris* cell.

16. The method of claim 10, wherein the heterologous EgtB comprises the amino acid sequence of SEQ ID NO: 2, the heterologous EgtC comprises the amino acid sequence of SEQ ID NO: 4, the heterologous EgtD comprises the amino acid sequence of SEQ ID NO: 6, and the heterologous EgtE comprises the amino acid sequence of SEQ ID NO: 8.

* * * * *

SEQUENCE LISTING

<160> NUMBER OF SEQ ID NOS: 16

<210> SEQ ID NO 1
<211> LENGTH: 1287
<212> TYPE: DNA
<213> ORGANISM: Artificial Sequence
<220> FEATURE:
<223> OTHER INFORMATION: synthetic

<400> SEQUENCE: 1

```
atgatcgcac gcgagacact ggccgacgag ctggccctgg cccgcgaacg cacgttgcgg      60
ctcgtggagt tcgacgacgc ggaactgcat cgccagtaca acccgctgat gagcccgctc     120
gtgtgggacc tcgcgcacat cgggcagcag gaagaactgt ggctgctgcg cgacggcaac     180
cccgaccgcc ccggcatgct cgcacccgag gtggaccggc tttacgacgc gttcgagcac     240
tcacgcgcca gccgggtcaa cctcccgttg ctgccgcctt cggatgcgcg cgcctactgc     300
gcgacggtgc gggccaaggc gctcgacacc ctcgacacgc tgcccgagga cgatccgggc     360
ttccggttcg cgctggtgat cagccacgag aaccagcacg acgagaccat gctgcaggca     420
ctcaacctgc gcgagggccc acccctgctc gacaccggaa ttcccctgcc cgcgggcagg     480
ccaggcgtgg caggcacgtc ggtgctggtg ccgggcggcc cgttcgtgct cggggtcgac     540
gcgctgaccg aaccgcactc actggacaac gaacggcccg cccacgtcgt ggacatcccg     600
tcgttccgga tcggccgcgt gccggtcacc aacgccgaat ggcgcgagtt catcgacgac     660
ggtggctacg accaaccgcg ctggtggtcg ccacgcggct gggcgcaccg ccaggaggcg     720
ggcctggtgg ccccgcagtt ctggaacccc gacggcaccc gcacccggtt cgggcacatc     780
gaggagatcc cgggtgacga acccgtgcag cacgtgacgt tcttcgaagc cgaggcctac     840
gcggcgtggg ccggtgctcg gttgcccacc gagatcgaat gggagaaggc ctgcgcgtgg     900
gatccggtcg ccggtgctcg cgccggttc ccctggggct cagcacaacc cagcgcggcg      960
ctggccaacc tcggcggtga cgcacgccgc ccggcgccgg tcggggccta cccggcgggg    1020
gcgtcggcct atggcgccga gcagatgctg ggcgacgtgt gggagtggac ctcctcgccg    1080
ctgcggccgt ggcccggttt cacgccgatg atctacgagc gctacagcac gccgttcttc    1140
gagggcacca catccggtga ctaccgcgtg ctgcgcggcg ggtcatgggc cgttgcaccg    1200
ggaatcctgc ggcccagctt ccgcaactgg gaccacccga tccggcggca gatattctcg    1260
ggtgtccgcc tggcctggga cgtctga                                        1287
```

<210> SEQ ID NO 2
<211> LENGTH: 428
<212> TYPE: PRT
<213> ORGANISM: Artificial Sequence
<220> FEATURE:
<223> OTHER INFORMATION: synthetic

<400> SEQUENCE: 2

```
Met Ile Ala Arg Glu Thr Leu Ala Asp Glu Leu Ala Leu Ala Arg Glu
1               5                   10                  15

Arg Thr Leu Arg Leu Val Glu Phe Asp Asp Ala Glu Leu His Arg Gln
                20                  25                  30

Tyr Asn Pro Leu Met Ser Pro Leu Val Trp Asp Leu Ala His Ile Gly
            35                  40                  45

Gln Gln Glu Glu Leu Trp Leu Leu Arg Asp Gly Asn Pro Asp Arg Pro
        50                  55                  60

Gly Met Leu Ala Pro Glu Val Asp Arg Leu Tyr Asp Ala Phe Glu His
```

```
                65                  70                  75                  80
        Ser Arg Ala Ser Arg Val Asn Leu Pro Leu Pro Pro Ser Asp Ala
                        85                  90                  95

Arg Ala Tyr Cys Ala Thr Val Arg Ala Lys Ala Leu Asp Thr Leu Asp
                        100                 105                 110

Thr Leu Pro Glu Asp Pro Gly Phe Arg Phe Ala Leu Val Ile Ser
                        115                 120                 125

His Glu Asn Gln His Asp Glu Thr Met Leu Gln Ala Leu Asn Leu Arg
                    130                 135                 140

Glu Gly Pro Pro Leu Leu Asp Thr Gly Ile Pro Leu Pro Ala Gly Arg
        145                 150                 155                 160

Pro Gly Val Ala Gly Thr Ser Val Leu Val Pro Gly Pro Phe Val
                            165                 170                 175

Leu Gly Val Asp Ala Leu Thr Glu Pro His Ser Leu Asp Asn Glu Arg
                        180                 185                 190

Pro Ala His Val Val Asp Ile Pro Ser Phe Arg Ile Gly Arg Val Pro
                        195                 200                 205

Val Thr Asn Ala Glu Trp Arg Glu Phe Ile Asp Asp Gly Gly Tyr Asp
                    210                 215                 220

Gln Pro Arg Trp Trp Ser Pro Arg Gly Trp Ala His Arg Gln Glu Ala
        225                 230                 235                 240

Gly Leu Val Ala Pro Gln Phe Trp Asn Pro Asp Gly Thr Arg Thr Arg
                            245                 250                 255

Phe Gly His Ile Glu Glu Ile Pro Gly Asp Glu Pro Val Gln His Val
                        260                 265                 270

Thr Phe Phe Glu Ala Glu Ala Tyr Ala Ala Trp Ala Gly Ala Arg Leu
                    275                 280                 285

Pro Thr Glu Ile Glu Trp Glu Lys Ala Cys Ala Trp Asp Pro Val Ala
                    290                 295                 300

Gly Ala Arg Arg Arg Phe Pro Trp Gly Ser Ala Gln Pro Ser Ala Ala
        305                 310                 315                 320

Leu Ala Asn Leu Gly Gly Asp Ala Arg Arg Pro Ala Pro Val Gly Ala
                            325                 330                 335

Tyr Pro Ala Gly Ala Ser Ala Tyr Gly Ala Glu Gln Met Leu Gly Asp
                        340                 345                 350

Val Trp Glu Trp Thr Ser Ser Pro Leu Arg Pro Trp Pro Gly Phe Thr
                    355                 360                 365

Pro Met Ile Tyr Glu Arg Tyr Ser Thr Pro Phe Phe Glu Gly Thr Thr
        370                 375                 380

Ser Gly Asp Tyr Arg Val Leu Arg Gly Gly Ser Trp Ala Val Ala Pro
        385                 390                 395                 400

Gly Ile Leu Arg Pro Ser Phe Arg Asn Trp Asp His Pro Ile Arg Arg
                        405                 410                 415

Gln Ile Phe Ser Gly Val Arg Leu Ala Trp Asp Val
                        420                 425
```

<210> SEQ ID NO 3
<211> LENGTH: 684
<212> TYPE: DNA
<213> ORGANISM: Artificial Sequence
<220> FEATURE:
<223> OTHER INFORMATION: synthetic

<400> SEQUENCE: 3
atgtgccggc atgtggcgtg gctgggcgcg ccgcggtcgt tggccgacct ggtgctcgac    60

```
ccgccgcagg gactgctggt gcagtcctac gcaccgcgac gacagaagca cggtctgatg      120
aacgccgacg gttggggcgc agggttttc gacgacgagg gagtggcccg ccgctggcgc       180
agcgacaaac cgctgtgggg tgatgcgtcg ttcgcgtcgg tggcacccgc actacgcagt      240
cgttgcgtgc tggccgcggt gcgctcggcc accatcggca tgcccatcga accgtcggcg      300
tcggcgccgt tcagcgacgg gcagtggctg ctgtcgcaca acggctggt cgaccgcggg       360 gtgctcccgt tgaccggtgc cgccgagtcc acggtggaca gcgcgatcgt cgcggcgctc      420
atcttctccc gtggcctcga cgcgctcggc gccaccatcg ccgaggtcgg cgaactcgac      480
ccgaacgcgc ggttgaacat cctggccgcc aacggttccc ggctgctcgc caccacctgg      540
ggggacacgc tgtcggtcct gcaccgcccc gacggcgtcg tcctcgcgag cgaaccctac      600
gacgacgatc ccggctggtc ggacatcccg gaccggcacc tcgtcgacgt ccgcgacgcc      660
cacgtcgtcg tgacacccct gtga                                             684
```

<210> SEQ ID NO 4  
<211> LENGTH: 227  
<212> TYPE: PRT  
<213> ORGANISM: Artificial Sequence  
<220> FEATURE:  
<223> OTHER INFORMATION: synthetic
<400> SEQUENCE: 4

```
Met Cys Arg His Val Ala Trp Leu Gly Ala Pro Arg Ser Leu Ala Asp
1               5                   10                  15

Leu Val Leu Asp Pro Pro Gln Gly Leu Leu Val Gln Ser Tyr Ala Pro
            20                  25                  30

Arg Arg Gln Lys His Gly Leu Met Asn Ala Asp Gly Trp Gly Ala Gly
        35                  40                  45

Phe Phe Asp Asp Glu Gly Val Ala Arg Arg Trp Arg Ser Asp Lys Pro
    50                  55                  60

Leu Trp Gly Asp Ala Ser Phe Ala Ser Val Ala Pro Ala Leu Arg Ser
65                  70                  75                  80

Arg Cys Val Leu Ala Ala Val Arg Ser Ala Thr Ile Gly Met Pro Ile
                85                  90                  95

Glu Pro Ser Ala Ser Ala Pro Phe Ser Asp Gly Gln Trp Leu Leu Ser
            100                 105                 110

His Asn Gly Leu Val Asp Arg Gly Val Leu Pro Leu Thr Gly Ala Ala
        115                 120                 125

Glu Ser Thr Val Asp Ser Ala Ile Val Ala Ala Leu Ile Phe Ser Arg
    130                 135                 140

Gly Leu Asp Ala Leu Gly Ala Thr Ile Ala Glu Val Gly Glu Leu Asp
145                 150                 155                 160

Pro Asn Ala Arg Leu Asn Ile Leu Ala Ala Asn Gly Ser Arg Leu Leu
                165                 170                 175

Ala Thr Thr Trp Gly Asp Thr Leu Ser Val Leu His Arg Pro Asp Gly
            180                 185                 190

Val Val Leu Ala Ser Glu Pro Tyr Asp Asp Pro Gly Trp Ser Asp
            195                 200                 205

Ile Pro Asp Arg His Leu Val Asp Val Arg Asp Ala His Val Val Val
        210                 215                 220

Thr Pro Leu
225
```

<210> SEQ ID NO 5
<211> LENGTH: 966
<212> TYPE: DNA
<213> ORGANISM: Artificial Sequence
<220> FEATURE:
<223> OTHER INFORMATION: synthetic

<400> SEQUENCE: 5

```
atgacgctct cactggccaa ctacctggca gccgactcgg ccgccgaagc actgcgccgt      60
gacgtccgcg cgggcctcac cgcggcaccg aagagtctgc cgcccaagtg gttctacgac     120
gccgtcggca gtgatctgtt cgaccagatc acccggctcc ccgagtatta ccccacccgc     180
accgaggcgc agatcctgcg gacccggtcg gcggagatca tcgcggccgc gggtgccgac     240
accctggtgg aactgggcag tggtacgtcg gagaaaaccc gcatgctgct cgacgccatg     300
cgcgacgccg agttgctgcg ccgcttcatc ccgttcgacg tcgacgcggg cgtgctgcgc     360
tcggccgggg cggcaatcgg cgcggagtac cccggtatcg agatcgacgc ggtatgtggc     420
gatttcgagg aacatctggg caagatcccg catgtcggac ggcggctcgt ggtgttcctg     480
gggtcgacca tcggcaacct gacacccgcg ccccgcgcgg agttcctcag tactctcgcg     540
gacacgctgc agccgggcga cagcctgctg ctgggcaccg atctggtgaa ggacaccggc     600
cggttggtgc gcgcgtacga cgacgcggcc ggcgtcaccg cggcgttcaa ccgcaacgtg     660
ctggccgtgg tgaaccgcga actgtccgcc gatttcgacc tcgacgcgtt cgagcatgtc     720
gcgaagtgga actccgacga ggaacgcatc gagatgtggt tgcgtgcccg caccgcacag     780
catgtccgcg tcgcggcact ggacctggag gtcgacttcg ccgcgggtga ggagatgctc     840
accgaggtgt cctgcaagtt ccgtcccgag aacgtcgtcg ccgagctggc ggaagccggt     900
ctgcggcaga cgcattggtg gaccgatccg gccggggatt tcgggttgtc gctggcggtg     960
cggtga                                                                966
```

<210> SEQ ID NO 6
<211> LENGTH: 321
<212> TYPE: PRT
<213> ORGANISM: Artificial Sequence
<220> FEATURE:
<223> OTHER INFORMATION: synthetic

<400> SEQUENCE: 6

```
Met Thr Leu Ser Leu Ala Asn Tyr Leu Ala Ala Asp Ser Ala Ala Glu
 1               5                  10                  15

Ala Leu Arg Arg Asp Val Arg Ala Gly Leu Thr Ala Ala Pro Lys Ser
            20                  25                  30

Leu Pro Pro Lys Trp Phe Tyr Asp Ala Val Gly Ser Asp Leu Phe Asp
        35                  40                  45

Gln Ile Thr Arg Leu Pro Glu Tyr Tyr Pro Thr Arg Thr Glu Ala Gln
    50                  55                  60

Ile Leu Arg Thr Arg Ser Ala Glu Ile Ile Ala Ala Gly Ala Asp
65                  70                  75                  80

Thr Leu Val Glu Leu Gly Ser Gly Thr Ser Glu Lys Thr Arg Met Leu
                85                  90                  95

Leu Asp Ala Met Arg Asp Ala Glu Leu Leu Arg Arg Phe Ile Pro Phe
            100                 105                 110

Asp Val Asp Ala Gly Val Leu Arg Ser Ala Gly Ala Ala Ile Gly Ala
        115                 120                 125

Glu Tyr Pro Gly Ile Glu Ile Asp Ala Val Cys Gly Asp Phe Glu Glu
    130                 135                 140
```

His Leu Gly Lys Ile Pro His Val Gly Arg Arg Leu Val Val Phe Leu
145                 150                 155                 160

Gly Ser Thr Ile Gly Asn Leu Thr Pro Ala Pro Arg Ala Glu Phe Leu
            165                 170                 175

Ser Thr Leu Ala Asp Thr Leu Gln Pro Gly Asp Ser Leu Leu Leu Gly
        180                 185                 190

Thr Asp Leu Val Lys Asp Thr Gly Arg Leu Val Arg Ala Tyr Asp Asp
    195                 200                 205

Ala Ala Gly Val Thr Ala Ala Phe Asn Arg Asn Val Leu Ala Val Val
210                 215                 220

Asn Arg Glu Leu Ser Ala Asp Phe Asp Leu Asp Ala Phe Glu His Val
225                 230                 235                 240

Ala Lys Trp Asn Ser Asp Glu Glu Arg Ile Glu Met Trp Leu Arg Ala
                245                 250                 255

Arg Thr Ala Gln His Val Arg Val Ala Ala Leu Asp Leu Glu Val Asp
            260                 265                 270

Phe Ala Ala Gly Glu Glu Met Leu Thr Glu Val Ser Cys Lys Phe Arg
        275                 280                 285

Pro Glu Asn Val Val Ala Glu Leu Ala Glu Ala Gly Leu Arg Gln Thr
    290                 295                 300

His Trp Trp Thr Asp Pro Ala Gly Asp Phe Gly Leu Ser Leu Ala Val
305                 310                 315                 320

Arg

<210> SEQ ID NO 7
<211> LENGTH: 1113
<212> TYPE: DNA
<213> ORGANISM: Artificial Sequence
<220> FEATURE:
<223> OTHER INFORMATION: synthetic

<400> SEQUENCE: 7
atgctcgcgc agcagtggcg tgacgcccgt cccaaggttg ccggggttgca cctggacagc      60 ggggcatgtt cgcggcagag cttcgcggtg atcgacgcga ccaccgcaca cgcacgccac     120
gaggccgagg tgggtggtta tgtggcggcc gaggctgcga cgccggcgct cgacgccggg     180
cgggccgcgc tcgcgtcgct catcggtttt gcggcgtcgg acgtggtgta caccagcgga     240
tccaaccacg ccatcgacct gttgctgtcg agctggccgg ggaagcgcac gctggcctgc     300
ctgcccggcg agtacgggcc gaatctgtct gccatggcgg ccaacggttt ccaggtgcgt     360
gcgctaccgg tcgacgacga cgggcgggtg ctggtcgacg aggcgtcgca cgaactgtcg     420
gcccatcccg tcgcgctcgt acacctcacc gcattggcaa gccatcgcgg gatcgcgcaa     480
cccgcggcag aactcgtcga ggcctgccac aatgcgggga tccccgtggt gatcgacgcc     540
gcgcaggcgc tggggcatct ggactgcaat gtcggggccg acgcggtgta ctcatcgtcg     600
cgcaagtggc tcgccggccc cgtggtgtc ggggtgctcg cggtgcggcc cgaactcgcc     660
gagcgtctgc aaccgcggat ccccccgtcc gactggccaa ttccgatgag cgtcttggag     720
aagctcgaac taggtgagca caacgcgcg gcgcgtgtgg gattctccgt cgcggttggt     780
gagcatctcg cagcagggcc cacggcggtg cgcgaacgac tcgccgaggt ggggcgtctc     840
tctcggcagg tgctggcaga ggtcgacggg tggcgcgtcg tcgaaccggt cgaccaaccc     900
accgcgatca ccacccttga gtccaccgat ggtgccgatc ccgcgtcggt gcgctcgtgg     960
ctgatcgcgg agcgtggcat cgtgaccacc gcgtgtgaac tcgcgcgggc accgttcgag    1020

```
atgcgcacgc cggtgctgcg aatctcgccg cacgtcgacg tgacggtcga cgaactggag   1080
cagttcgccg cagcgttgcg tgaggcgccc tga                                1113
```

<210> SEQ ID NO 8
<211> LENGTH: 370
<212> TYPE: PRT
<213> ORGANISM: Artificial Sequence
<220> FEATURE:
<223> OTHER INFORMATION: synthetic

<400> SEQUENCE: 8

```
Met Leu Ala Gln Gln Trp Arg Asp Ala Arg Pro Lys Val Ala Gly Leu
1               5                   10                  15

His Leu Asp Ser Gly Ala Cys Ser Arg Gln Ser Phe Ala Val Ile Asp
            20                  25                  30

Ala Thr Thr Ala His Ala Arg His Glu Ala Glu Val Gly Gly Tyr Val
        35                  40                  45

Ala Ala Glu Ala Ala Thr Pro Ala Leu Asp Ala Gly Arg Ala Ala Val
    50                  55                  60

Ala Ser Leu Ile Gly Phe Ala Ala Ser Asp Val Val Tyr Thr Ser Gly
65                  70                  75                  80

Ser Asn His Ala Ile Asp Leu Leu Ser Ser Trp Pro Gly Lys Arg
            85                  90                  95

Thr Leu Ala Cys Leu Pro Gly Glu Tyr Gly Pro Asn Leu Ser Ala Met
            100                 105                 110

Ala Ala Asn Gly Phe Gln Val Arg Ala Leu Pro Val Asp Asp Asp Gly
            115                 120                 125

Arg Val Leu Val Asp Glu Ala Ser His Glu Leu Ser Ala His Pro Val
    130                 135                 140

Ala Leu Val His Leu Thr Ala Leu Ala Ser His Arg Gly Ile Ala Gln
145                 150                 155                 160

Pro Ala Ala Glu Leu Val Glu Ala Cys His Asn Ala Gly Ile Pro Val
                165                 170                 175

Val Ile Asp Ala Ala Gln Ala Leu Gly His Leu Asp Cys Asn Val Gly
            180                 185                 190

Ala Asp Ala Val Tyr Ser Ser Arg Lys Trp Leu Ala Gly Pro Arg
    195                 200                 205

Gly Val Gly Val Leu Ala Val Arg Pro Glu Leu Ala Glu Arg Leu Gln
210                 215                 220

Pro Arg Ile Pro Pro Ser Asp Trp Pro Ile Pro Met Ser Val Leu Glu
225                 230                 235                 240

Lys Leu Glu Leu Gly Glu His Asn Ala Ala Arg Val Gly Phe Ser
                245                 250                 255

Val Ala Val Gly Glu His Leu Ala Ala Gly Pro Thr Ala Val Arg Glu
            260                 265                 270

Arg Leu Ala Glu Val Gly Arg Leu Ser Arg Gln Val Leu Ala Glu Val
    275                 280                 285

Asp Gly Trp Arg Val Val Glu Pro Val Asp Gln Pro Thr Ala Ile Thr
290                 295                 300

Thr Leu Glu Ser Thr Asp Gly Ala Asp Pro Ala Ser Val Arg Ser Trp
305                 310                 315                 320

Leu Ile Ala Glu Arg Gly Ile Val Thr Thr Ala Cys Glu Leu Ala Arg
                325                 330                 335

Ala Pro Phe Glu Met Arg Thr Pro Val Leu Arg Ile Ser Pro His Val
```

```
                340                 345                 350
Asp Val Thr Val Asp Glu Leu Glu Gln Phe Ala Ala Ala Leu Arg Glu
            355                 360                 365

Ala Pro
    370
```

<210> SEQ ID NO 9
<211> LENGTH: 49
<212> TYPE: DNA
<213> ORGANISM: Artificial Sequence
<220> FEATURE:
<223> OTHER INFORMATION: synthetic

<400> SEQUENCE: 9
agaattcaaa agatctaaag gaggccatcc atgatcgcac gcgagacac         49

<210> SEQ ID NO 10
<211> LENGTH: 53
<212> TYPE: DNA
<213> ORGANISM: Artificial Sequence
<220> FEATURE:
<223> OTHER INFORMATION: synthetic

<400> SEQUENCE: 10
actcgagttt ggatcctcag acgtcccagg ccaggcggac acccgagaat atc     53

<210> SEQ ID NO 11
<211> LENGTH: 50
<212> TYPE: DNA
<213> ORGANISM: Artificial Sequence
<220> FEATURE:
<223> OTHER INFORMATION: synthetic

<400> SEQUENCE: 11
agaattcaaa agatctaaag gaggccatcc atgtgccggc atgtggcgtg         50

<210> SEQ ID NO 12
<211> LENGTH: 34
<212> TYPE: DNA
<213> ORGANISM: Artificial Sequence
<220> FEATURE:
<223> OTHER INFORMATION: synthetic

<400> SEQUENCE: 12
actcgagttt ggatcctcac aggggtgtca cgac                         34

<210> SEQ ID NO 13
<211> LENGTH: 51
<212> TYPE: DNA
<213> ORGANISM: Artificial Sequence
<220> FEATURE:
<223> OTHER INFORMATION: synthetic

<400> SEQUENCE: 13
agaattcaaa agatctaaag gaggccatcc atgacgctct cactggccaa c       51

<210> SEQ ID NO 14
<211> LENGTH: 35
<212> TYPE: DNA
<213> ORGANISM: Artificial Sequence
<220> FEATURE:
<223> OTHER INFORMATION: synthetic

<400> SEQUENCE: 14
actcgagttt ggatcctcac cgcaccgcca gcgac                        35

```
<210> SEQ ID NO 15
<211> LENGTH: 47
<212> TYPE: DNA
<213> ORGANISM: Artificial Sequence
<220> FEATURE:
<223> OTHER INFORMATION: synthetic

<400> SEQUENCE: 15
agaattcaaa agatctaaag gaggccatcc atgctcgcgc agcagtg         47

<210> SEQ ID NO 16
<211> LENGTH: 35
<212> TYPE: DNA
<213> ORGANISM: Artificial Sequence
<220> FEATURE:
<223> OTHER INFORMATION: synthetic

<400> SEQUENCE: 16
actcgagttt ggatcctcag ggcgcctcac gcaac                      35
```